United States Patent
Meng et al.

(10) Patent No.: US 7,279,598 B2
(45) Date of Patent: Oct. 9, 2007

(54) PROCESS FOR SEPARATING AND RECOVERING 3-HYDROXYPROPIONIC ACID AND ACRYLIC ACID

(76) Inventors: Xiangsheng Meng, 417 Santa Fe Trail, Chanhassen, MN (US) 55317; Paraskevas Tsobanakis, 8579 Birch Blvd., Inver Grove Heights, MN (US) 55076; Jeffrey Malsam, 3109 Freemont Ave., South, Minneapolis, MN (US) 55408; Timothy Abraham, 18507 Apple Tree Ct., Minnetonka, MN (US) 55345

( * ) Notice: Subject to any disclaimer, the term of this patent is extended or adjusted under 35 U.S.C. 154(b) by 0 days.

(21) Appl. No.: 10/560,949

(22) PCT Filed: Jun. 25, 2004

(86) PCT No.: PCT/US2004/020580

§ 371 (c)(1),
(2), (4) Date: Dec. 15, 2005

(87) PCT Pub. No.: WO2005/003074

PCT Pub. Date: Jan. 13, 2005

(65) Prior Publication Data

US 2007/0027342 A1    Feb. 1, 2007

Related U.S. Application Data

(60) Provisional application No. 60/482,815, filed on Jun. 26, 2003.

(51) Int. Cl.
*C07C 51/42* (2006.01)
(52) U.S. Cl. .................................... 562/580; 562/600
(58) Field of Classification Search ................ 562/580, 562/600
See application file for complete search history.

(56) References Cited

U.S. PATENT DOCUMENTS

| | | |
|---|---|---|
| 5,705,688 A | 1/1998 | Fauconet et al. |
| 6,180,827 B1 | 1/2001 | Lee et al. |
| 6,281,386 B1 | 8/2001 | Fauconet et al. |

FOREIGN PATENT DOCUMENTS

GB        1167793        * 10/1969

* cited by examiner

*Primary Examiner*—Eyle Yvonne
*Assistant Examiner*—Sudhaker Katakam

(57) ABSTRACT

Disclosed is a process for separating and recovering 3-hydroxypropionic acid from an aqueous solution comprising 3-hydroxypropionic acid and acrylic acid, comprising counter current extracting the aqueous solution with ethyl acetate extractant. Further disclosed is a process for separating and recovering 3-hydroxypropionic acid and acrylic acid from an aqueous solution comprising 3-hydroxypropionic acid and acrylic acid.

7 Claims, No Drawings

PROCESS FOR SEPARATING AND RECOVERING 3-HYDROXYPROPIONIC ACID AND ACRYLIC ACID

CROSS REFERENCE TO RELATED APPLICATIONS

This is the U.S. National Stage of International Application No. PCT/US2004/020580, filed Jun. 25, 2004, which in turn claims the benefit of U.S. Provisional Application No. 60/482,815 filed Jun. 26, 2003, the entire contents of which are incorporated herein by reference.

FIELD

This invention relates to a process for separating and recovering 3-hydroxypropionic acid from an aqueous solution comprising 3-hydroxypropionic acid, acrylic acid and/or other acid impurities. The aqueous solution may be obtained from anyone of multiple preparation routes of 3-hydroxypropionic acid, including hydration of acrylic acid.

Furthermore, the invention relates to combining both the process for separating and recovering 3-hydroxypropionic acid and a process for separating and recovering acrylic acid. This allows for the recycling of acrylic acid, and organic extractant, providing economic advantages. The processes for separating and recovering acrylic acid from solutions comprising acrylic acid and an organic extractant are as follows. In a first process, a solution comprising acrylic acid and an organic extractant is subjected to back extraction with water to recover the acrylic acid from the extractant. In another process, a solution comprising acrylic acid and an organic extractant having a boiling point lower than 100° C. is distilled in the presence of water to distill the extractant, resulting in an aqueous acrylic acid solution.

BACKGROUND

Various methods for separating and recovering 3-hydroxypropionic acid from an aqueous solution comprising 3-hydroxypropionic acid and acrylic acid are known. Included within such methods is distilling acrylic acid from the aqueous solution. Further, it is known that acrylic acid in the aqueous solution is extracted with ethyl acetate as an extractant in a cross current manner. This is described in a publication by Shem, Changzhou, You, Sihui; Huaxueshijie, 1997, 19 (2), pg 77-79.

SUMMARY

The present invention provides batch and continuous processes for separating and recovering 3-hydroxypropionic acid from an aqueous solution comprising 3-hydroxypropionic acid, acrylic acid and/or other acid impurities by a counter current mode solvent extraction with ethyl acetate as the organic extractant, that allows for separation and recovery of 3-hydroxypropionic acid. In addition, the present invention provides a process for separating and recovering 3-hydroxypropionic acid in high efficiency, at a high yield, and at high purity.

Additionally, the present invention provides a process for separating and recovering 3-hydroxypropionic acid from an aqueous solution comprising 3-hydroxypropionic acid, acrylic acid, and/or other acid impurities, that also includes the separation and recovery of acrylic acid from solutions comprising acrylic acid and an organic extractant, and regenerating extractant for reuse.

In one embodiment the present invention provides a process for extracting acrylic acid and/or other acid impurities from an aqueous solution also containing 3-hydroxypropionic acid with ethyl acetate extractant using a counter current manner. Acrylic acid may be recovered from the extractant thereby enabling the extractant and acrylic acid to be recycled for reuse. The aqueous solution remaining after acrylic acid extraction by the ethyl acetate extractant comprises 3-hydroxypropionic acid. The extraction is conducted in a counter current manner utilizing any equipment such that the separation and recovery of 3-hydroxypropionic acid from acrylic acid can be achieved.

Another embodiment of the present invention comprises combining the process for separating and recovering 3-hydroxypropionic acid from a solution comprising 3-hydroxypropionic acid and acrylic acid, utilizing a counter current mode extraction with ethyl acetate, with a process for separating and recovering acrylic acid from a solution comprising acrylic acid and ethyl acetate extractant. This combined process allows for recovering and recycling acrylic acid and/or extractant, providing economic advantage. These are two processes for separating and recovering acrylic acid from a solution comprising acrylic acid and ethyl acetate extractant. A first process comprises subjecting a solution comprising acrylic acid and extractant to back extraction with water, using any conventional technique, to separate and recover the acrylic acid from the extractant. A second process for separating and recovering acrylic acid from a solution comprising acrylic acid and ethyl acetate extractant comprises distilling the solution, in the presence of water, to distill the extractant, thereby resulting in an aqueous acrylic acid solution.

The 3-hydroxypropionic acid recovered by the present process is a known compound having many applications, and the product herein is useful in such applications. In particular, 3-hydroxypropionic acid is known to be useful in the preparation of polymeric materials, and as being useful intermediates in the preparation of various organic materials.

DETAILED DESCRIPTION

In accordance with the present invention, it has been found that the above and still further objects are achieved by counter current mode extracting acrylic acid and/or other acid impurities from an aqueous solution also containing 3-hydroxypropionic acid with an ethyl acetate as the organic extractant. Acrylic acid may be recovered from the organic extractant thereby enabling the organic extractant and acrylic acid to be recycled for reuse. The aqueous solution remaining after acrylic acid extraction by the organic extractant comprises 3-hydroxypropionic acid.

The extraction is conducted in a counter current manner, utilizing any equipment such that the separation and recovery of 3-hydroxypropionic acid from acrylic acid can be achieved.

Another embodiment of the present invention comprises combining the process for separating and recovering 3-hydroxypropionic acid from a solution comprising 3-hydroxypropionic acid and acrylic acid, utilizing a counter current mode extraction with ethyl acetate, with a process for separating and recovering acrylic acid from a solution comprising acrylic acid and ethyl acetate extractant. This combined process allows for recovering and recycling acrylic acid and/or extractant, providing economic advantage. There are two exemplary processes for separating and recovering acrylic acid from a solution comprising acrylic acid and ethyl acetate extractant. A first process comprises subjecting a solution comprising acrylic acid and extractant to back extraction with water, using any conventional technique, to separate and recover the acrylic acid from the extractant. A second process for separating and recovering acrylic acid from a solution comprising acrylic acid and ethyl acetate extractant comprises distilling the solution, in the presence of water, to distill the extractant, thereby resulting in an aqueous acrylic acid solution.

In the process for separating and recovering the 3-hydroxypropionic acid by counter current mode extraction from the solution comprising 3-hydroxypropionic acid and acrylic acid, the ethyl acetate for acrylic acid extraction in the organic phase is present in an amount of about 1 to about 100 weight percent. The remainder of the component in the organic phase is a saturated or unsaturated hydrocarbon solvent.

The counter current extraction of acrylic acid and/or other acid impurities, from the solution comprising 3-hydroxypropionic acid, is carried out at a temperature ranging from about 0° C. to about 70° C., preferably from about 20° C. to about 40° C., and more preferably from about 20° C. to about 25° C. The volume ratio of the organic phase to the aqueous phase in the extraction stage ranges from about 20:1 to about 1:20, preferably from about 10:1 to about 1:10, and more preferably from about 5:1 to about 1:5. The extraction is carried out in counter current manner and utilizes any extraction apparatus. The extraction is carried out for any period of time such that the extraction is achieved. For example, the extraction may be carried out in a multistage extraction column, in a counter current manner.

Remaining after the aqueous phase comprising the 3-hydroxypropionic acid is separated, is an organic phase that comprises acrylic acid and/or other acid impurities, and ethyl acetate extractant In one embodiment for separating and recovering the acrylic acid from the solution comprising acrylic acid and extractant, the solution is back extracted with water. Accordingly, the acrylic acid is recovered from the organic phase, and the ethyl acetate extractant is regenerated. The regenerated extractant may be recycled for use in the separation and recovery of the 3-hydroxypropionic acid. The back extraction of the acrylic acid ethyl acetate extractant solution is carried out at a temperature ranging from about 0° C. to about 180° C., preferably from about 50° C. to about 140° C. The volume ratio of the organic phase to the aqueous phase ranges from about 20:1 to about 1:20, preferably from about 10:1 to about 1:10, and more preferably from about 5:1 to about 1:5. The back extraction with water is carried out in any manner and with any extraction equipment in any period of time such that the back extraction is achieved. For example, the back extraction may be carried out in a multistage extraction column in counter current, co-current or cross current manner.

In another embodiment for separating and recovering acrylic acid from a solution comprising acrylic acid, ethyl acetate extractant and/or other acid impurities, the organic phase that contains mainly acrylic acid and other acid impurities is subjected to distillation of ethyl acetate extractant, in the presence of water. The distilled extractant may be recycled back to the extraction for reuse to extract acrylic acid. The distillation of extractant may be carried out, in the presence of water, in accordance with any manner, under any conditions, such that the distillation is achieved. For example, the distillation of extractant may be carried out at any pressure, and at any temperature. The volume ratio of the organic phase to the aqueous phase in the extraction stage ranges from about 20:1 to about 1:20, preferably from about 10:1 to about 1:10, and more preferably from about 5:1 to about 1:5.

The counter current extraction is carried out in accordance with any manner and with any extraction equipment in any period of time such that the extraction is achieved. For example, the extraction may be carried out in a multistage extraction column in counter current manner. The distillation of extractant may be carried out in accordance with any manner at any conditions such that the distillation is achieved.

The process for separating and recovering 3-hydroxypropionic acid herein by counter current solvent extraction using ethyl acetate, from a solution comprising 3-hydroxypropionic acid, acrylic acid and/or other acid impurities, may be combined with any of the processes herein for separating and recovering acrylic acid from ethyl acetate extractant solutions containing the acrylic acid. The processes may be combined in any manner to provide an economic advantage by allowing recovery and reuse of acrylic acid and extractant.

It has been found that the present process of solvent extraction with ethyl acetate in a counter current manner results in a usage of ethyl acetate that is about five (5) times less than the amount of ethyl acetate utilized when the extraction is carried out in cross current manner.

The invention will be more readily understood by reference to the following examples. There are, of course, many other forms of this invention which will become obvious to one skilled in the art, once the invention has been fully disclosed, and it will accordingly be recognized that these examples are given for the purpose of illustration only, and are not to be construed as limiting the scope of this invention in any way.

EXAMPLES

In the following examples, products are analyzed by high pressure liquid chromatography (HPLC), described as follows:

High Pressure Liquid Chromatography (HPLC)

HPLC—the products produced by the process are analyzed using a Waters 1525 Binary HPLC pump, equipped with a Waters 717 plus Autosampler, and Waters 2410 Refractive Index and Waters 2487 Dual Lambda Absorbance detectors, having a Bio-Rad HP87-H column, 0.004 N sulfuric acid as the mobile phase, a flow rate of 0.6 ml/min, and a column temperature of 60° C.

Example 1

In this example, there were utilized five (5) aqueous stock solutions. The aqueous stock solutions comprise 30% 3-hydroxypropionic acid aqueous solution and 99% acrylic acid. In each of the five aqueous stock solutions, the concentration of 3-hydroxypropionic acid is approximately two times higher than the concentration of the acrylic acid. The aqueous stock solutions are shown in the following Table 1.

TABLE 1

Concentration of acrylic acid and 3-hydroxypropionic acid in stock solutions.

| Aqueous Stock Solution No. | Conc. of acrylic acid in stock solution, wt. % | Conc. of 3-hydroxypropionic acid in stock solution, wt. % | Conc. of total acids in stock solution, wt. % |
| --- | --- | --- | --- |
| 1 | 0.67 | 1.34 | 2.01 |
| 2 | 3.33 | 6.67 | 10.00 |
| 3 | 6.67 | 13.34 | 20.01 |
| 4 | 9.99 | 19.98 | 29.97 |
| 5 | 12.51 | 25.05 | 37.56 |

The extraction procedure utilized in Examples 1-5 for separating and recovering 3-hydroxypropionic acid and acrylic acid from aqueous solutions comprising 3-hydroxypropionic acid and acrylic acid is carried out as follows:

1. To a 15 ml centrifuge tube 5 ml of each acid stock solution and ethyl acetate extractant were added. Masses of the empty centrifuge tube, the aqueous solution and extractant were recorded.
2. The tube was placed on a platform shaker and the contents in the tube were mixed at 230 rpm for 30 minutes at 22° C. (rpm designates revolutions per minute).
3. At the end of mixing, the tube was centrifuged at 4500 rpm for 5 minutes.
4. The volumes of the aqueous and ethyl acetate extractant phases in the tubes were recorded.
5. The aqueous phase was separated from the ethyl acetate extractant phase and the masses of both phases were recorded.
6. The acrylic acid and the 3-hydroxypropionic acid in the aqueous solution were analyzed by HPLC.
7. The concentrations of acrylic acid and 3-hydroxypropionic acid in the ethyl acetate extractant were calculated by subtracting the concentrations of acrylic acid and 3-hydroxypropionic acid in the aqueous phase from the initial concentration in the stock solution.

The processing conditions and experimental results for the extraction of acrylic acid (AA) and 3-hydroxypropionic acid (3HP) by ethyl acetate are reported in the following Table 2.

Comparison of Countercurrent Extraction with Crosscurrent Extraction

A comparison between a countercurrent extraction and a crosscurrent extraction with ethyl acetate as extractant for the separation and recovery of 3-hydroxpropionic acid was done through calculation by using the known method published in the literature (L. Alders, "Liquid-Liquid Extraction; Theory and Laboratory Practice", second, revised edition, Elsevier Publishing, 1959, page 103-106). In the calculation the following assumptions were made:

1. Partition coefficients, D, for both acrylic acid and 3HP were assumed to be constants and an average number of partition coefficients listed in Table 2 was used. For acrylic acid, $D_{AA}=2.572$ and for 3HP, $D_{3HP}=0.274$.
2. Phase ratio, R, equals extractant flow rate divided by aqueous flow rate.
3. Solubilities of aqueous phase into extractant phase and extractant phase into aqueous phase that may change the flow rate of each phase were not considered in the calculation of phase ratio, R.
4. An initial aqueous solution contains 20 wt % of 3HP and 10 wt % acrylic acid.

Extraction factor for acrylic acid at each stage was calculated by using $E_{AA}=D_{AA} \times R$ and extraction factor for 3HP at each stage was calculated by using a formula of $E_{3HP}=D_{3HP} \times R$.

For crosscurrent extraction, the fraction for acrylic acid not extracted at each stage is calculated by a formula of $F_{AA}=1/(E_{AA}+1)$ in which $E_{AA}$ is extraction factor for acrylic acid at each stage.

For crosscurrent extraction, the fraction for 3HP not extracted at each stage is calculated by a formula of $F_{3HP}=1/(E_{3HP}+1)$ in which $E_{3HP}$ is extraction factor for 3HP at each stage.

For countercurrent extraction, the fraction for acrylic acid not extracted at each stage is calculated by a formula of $F_{AA}=(E_{AA}-1)/(E_{AA}^{a+1}-1)$ in which $E_{AA}$ is extraction factor for acrylic acid at each stage and $E_{AA}^{n+1}$ is n+1 power of extraction factor for acrylic acid at each stage, where n=number of stage (for example, at first stage n=1 and at second stage n=2, and the like).

For countercurrent extraction, the fraction for 3HP not extracted at each stage is calculated by a formula of $F_{3HP}=(E_{3HP}-1)/(E_{3HP}^{n+1}-1)$ in which $E_{3HP}$ is extraction factor for

TABLE 2

Extraction of Acrylic Acid (AA) and 3-Hydroxypropionic Acid (3HP) from aqueous stock solutions Containing AA and 3HP by Ethyl Acetate

| Example No. | Aqueous Stock Solution, No. | Acid in Aqueous Phase, wt % | | Acid in Ethyl Acetate Extractant Phase, wt % | | Partition Coefficient, $D^1$ | | Separation Factor, $S^2$ |
| --- | --- | --- | --- | --- | --- | --- | --- | --- |
| | | AA | 3HP | AA | 3HP | AA | 3HP | AA/3HP |
| 1 | 1 | 0.20 | 1.13 | 0.59 | 0.20 | 2.96 | 0.18 | 16.55 |
| 2 | 2 | 0.97 | 5.77 | 2.87 | 1.21 | 2.97 | 0.21 | 14.18 |
| 3 | 3 | 2.02 | 11.38 | 5.36 | 3.09 | 2.66 | 0.27 | 9.79 |
| 4 | 4 | 3.18 | 17.08 | 7.53 | 5.17 | 2.36 | 0.30 | 7.81 |
| 5 | 5 | 4.22 | 21.16 | 8.07 | 8.68 | 1.91 | 0.41 | 4.66 |

[1] Partition coefficient, D, was calculated by dividing the acid concentration in the ethyl acetate extractant phase by the acid concentration in the aqueous phase, for AA and 3HP.
[2] Separation factor, S, was calculated by dividing the partition coefficient of the acrylic acid by the partition coefficient of 3HP.

3HP at each stage and $E_{3HP}^{n+1}$ is n+1 power of extraction factor for 3HP at each stage, where n=number of stage (for example, at first stage n=1 and at second stage n=2, and the like).

The results of the calculation by applying the above assumptions and formulas are presented in the following Table 3-6.

TABLE 3

Crosscurrent Extraction of 3HP and Acrylic Acid with Ethyl Acetate

| Stage | Fraction not extracted for 3HP | Fraction not extracted for AA | 3HP purity, % | 3HP yield, % |
|---|---|---|---|---|
| 0 | | | 66.67 | 100.00 |
| 1 | 0.773 | 0.266 | 85.31 | 77.33 |
| 2 | 0.773 | 0.266 | 94.40 | 59.80 |
| 3 | 0.773 | 0.266 | 98.00 | 46.24 |
| 4 | 0.773 | 0.266 | 99.30 | 35.76 |
| 5 | 0.773 | 0.266 | 99.76 | 27.65 |
| 6 | 0.773 | 0.266 | 99.92 | 21.38 |

TABLE 4

Countercurrent Extraction of 3HP and Acrylic Acid with Ethyl Acetate

| Stage | Fraction not extracted for 3HP | Fraction not extracted for AA | 3HP purity, % | 3HP yield, % |
|---|---|---|---|---|
| 0 | | | 66.67 | 100.00 |
| 1 | 0.773 | 0.266 | 85.31 | 77.33 |
| 2 | 0.725 | 0.088 | 94.27 | 72.51 |
| 3 | 0.712 | 0.031 | 97.87 | 71.21 |
| 4 | 0.708 | 0.011 | 99.22 | 70.84 |
| 5 | 0.707 | 0.004 | 99.72 | 70.73 |
| 6 | 0.707 | 0.001 | 99.90 | 70.70 |

Table 3 is an example of six-stage crosscurrent extraction with an aqueous flow rate of 1000 kg/hr and an extractant flow rate of 1070 kg/hr. The aqueous solution contains 20% 3-hydroxypropionic acid and 10% acrylic acid. After six stages of crosscurrent extraction the 3HP product reaches a purity of 99.92% with a yield of 21.38%. A usage of ethyl acetate in the six stages of crosscurrent extraction is 6420 kg/hr.

While in an identical run as in crosscurrent extraction, a six-stage countercurrent extraction as showed in Table 4 produces the 3BP product having the same purity of 99.90% with a yield of 70.70% (3.3 times higher than one in crosscurrent extraction). A usage of ethyl acetate in the six stages of countercurrent extraction is 1070 kg/hr (6 times less than one in crosscurrent extraction).

Table 5 and Table 6 show a comparison of crosscurrent extraction with countercurrent extraction with about the same yield of 3HP product and the same amount of ethyl acetate extractant, but the product purity only reaches 88.37% after six stages of crosscurrent extraction. The 3HP product after six stages of countercurrent extraction reaches a purity of 99.01%.

TABLE 5

Crosscurrent Extraction of 3HP and Acrylic Acid with Ethyl Acetate

| Stage | Fraction not extracted for 3HP | Fraction not extracted for AA | 3HP purity, % | 3HP yield, % |
|---|---|---|---|---|
| 0 | 0.970 | 0.777 | 66.67 | 100.00 |
| 1 | 0.970 | 0.777 | 71.42 | 97.03 |
| 2 | 0.970 | 0.777 | 75.73 | 94.15 |
| 3 | 0.970 | 0.777 | 79.59 | 91.36 |
| 4 | 0.970 | 0.777 | 82.97 | 88.64 |
| 5 | 0.970 | 0.777 | 85.88 | 86.01 |
| 6 | 0.970 | 0.777 | 88.37 | 83.46 |

TABLE 6

Countercurrent Extraction of 3HP and Acrylic Acid with Ethyl Acetate

| Stage | Fraction not extracted for 3HP | Fraction not extracted for AA | 3HP purity, % | 3HP yield, % |
|---|---|---|---|---|
| 0 | | | 66.67 | 100.00 |
| 1 | 0.845 | 0.367 | 82.16 | 84.49 |
| 2 | 0.822 | 0.175 | 90.35 | 82.15 |
| 3 | 0.817 | 0.092 | 94.65 | 81.73 |
| 4 | 0.817 | 0.051 | 96.98 | 81.66 |
| 5 | 0.816 | 0.029 | 98.28 | 81.65 |
| 6 | 0.816 | 0.016 | 99.01 | 81.64 |

Example 2

This example shows the distillation of ethyl acetate loaded with acrylic acid. In a 100 ml round bottom flask is placed 18.5 grams ethyl acetate, 3 grams of acrylic acid and 9 grams of distilled water. Reduced pressure (about 100 mmHg) is applied to the flask for the distillation of ethyl acetate at room temperature (about 20-24° C.). The distillation is completed in about 5 minutes. Both the ethyl acetate distillate collected and the remaining aqueous solution in the flask are weighed and the concentrations of acrylic acid in both ethyl acetate distillate and the aqueous solution are determined by means of titration. The amount of acrylic acid remaining in the flask as the aqueous solution is 91%. About 7% acrylic acid is co-distilled with ethyl acetate with a small portion of water.

Example 3

An aqueous solution containing 10 wt % acrylic acid and 20 wt % 3-hydroxypropionic acid is fed into a six-stage countercurrent extraction column at a flow rate of 1000 kg/hr. Ethyl acetate extractant is fed into the six-stage countercurrent extraction column at a flow rate of 1070 kg/hr. After six stage countercurrent extraction, the aqueous stream is expected to contain 3-hydroxypropionic acid product with 99.9% purity. The yield of 3-hydroxypropionic acid product is expected to be 70.70%. After the six stage countercurrent extraction the ethyl acetate extractant stream is expected to contain about 9.3 wt % acrylic acid and 5.5 wt % 3-hydroxypropionic acid.

The above acrylic acid and 3-hydroxypropionic acid loaded ethyl acetate stream is mixed with distilled water at a ratio of 10 to 3 (extractant to water), and introduced into a container. The ethyl acetate is removed by distillation at a reduced pressure of about 100 mm Hg, and room temperature. The aqueous solution remaining in the flask is expected to contain about 21 wt % acrylic acid and about 12 wt % 3-hydroxypropionic acid. The aqueous solution of acrylic acid and 3-hydroxypropionic acid, and the distilled ethyl acetate are recycled.

The invention has been described above in detail with particular reference to specific embodiments thereof, but it will be understood that variations and modifications other than as specifically described herein can be effected within the spirit and scope of the invention.

What is claimed is:

1. A process comprising separating and recovering 3-hydroxypropionic acid from an aqueous solution comprising 3-hydroxypropionic acid and acrylic acid, via counter currently extracting the aqueous solution with an organic phase comprising ethyl acetate extractant.

2. The process according to claim 1, wherein the ethyl acetate extractant is present in the organic phase in an amount ranging from about 1 to about 100 weight percent.

3. The process according to claim 1, wherein, without further purification, the recovered 3-hydroxypropionic acid is at least about 80% pure when separated from the aqueous solution.

4. The process according to claim 1, wherein the volume ratio of organic phase to aqueous solution ranges from about 20:1 to about 1:20.

5. A process comprising separating and recovering 3-hydroxypropionic acid and acrylic acid from an aqueous solution comprising 3-hydroxypropionic acid and acrylic acid, including:

(a) counter currently extracting the aqueous solution with an organic phase comprising ethyl acetate to extract the acrylic acid from the aqueous phase and into the organic phase and to separate the acrylic acid from the 3-hydroxypropionic acid; and (b) contacting the organic phase formed in step (a) with water to extract the acrylic acid from the organic phase and into the water.

6. The process according to claim 5, wherein the ethyl acetate is present in the organic phase in an amount ranging from about 1 to about 100 weight percent.

7. A process comprising separating and recovering 3-hydroxypropionic acid and acrylic acid from an aqueous solution comprising 3-hydroxypropionic acid and acrylic acid, including:

(a) counter currently extracting the aqueous solution with an organic phase comprising ethyl acetate, to extract the acrylic acid from the aqueous solution into the organic phase and to separate the acrylic acid from the 3-hydroxypropionic acid; and (b) heating the organic phase formed in step (a), in the presence of water, to distill off the ethyl acetate, thereby forming an aqueous acrylic acid solution.

* * * * *

UNITED STATES PATENT AND TRADEMARK OFFICE
CERTIFICATE OF CORRECTION

PATENT NO. : 7,279,598 B2
APPLICATION NO. : 10/560949
DATED : October 9, 2007
INVENTOR(S) : Xiangsheng Meng et al.

Page 1 of 1

It is certified that error appears in the above-identified patent and that said Letters Patent is hereby corrected as shown below:

In the Specification:
  Column 6, line 37, "$a^{+1}$" should read --$n^{+1}$--.

Signed and Sealed this

Twenty-seventh Day of January, 2009

JOHN DOLL
*Acting Director of the United States Patent and Trademark Office*